United States Patent [19]
Amano

[11] Patent Number: 5,643,249
[45] Date of Patent: Jul. 1, 1997

[54] OPTICAL OPHTHALMIC TREATMENT APPARATUS

[75] Inventor: Masanori Amano, Gamagori, Japan

[73] Assignee: Nidek Co., Ltd., Japan

[21] Appl. No.: 401,288

[22] Filed: Mar. 9, 1995

Related U.S. Application Data

[63] Continuation of Ser. No. 16,973, Feb. 12, 1993, abandoned.

[30] Foreign Application Priority Data

Feb. 14, 1992 [JP] Japan .................. 4-014406 U

[51] Int. Cl.$^6$ .................................................. A61B 17/36
[52] U.S. Cl. .................................................. 606/4
[58] Field of Search .................. 606/4–6, 10–12

[56] References Cited

U.S. PATENT DOCUMENTS

| | | | |
|---|---|---|---|
| 3,703,176 | 11/1972 | Vassiliadis et al. | 606/4 |
| 3,796,220 | 3/1974 | Bredemeier | 606/4 |
| 3,828,788 | 8/1974 | Krasnov et al. | 606/4 |
| 4,397,310 | 8/1983 | Pomerantzeff | 606/4 X |
| 4,443,075 | 4/1984 | Crane | 606/4 |
| 4,776,335 | 10/1988 | Nakanishi et al. | 606/17 |
| 4,911,711 | 3/1990 | Telfair et al. | 606/4 |
| 4,931,053 | 6/1990 | L'Esperance, Jr. | 606/4 |
| 5,163,934 | 11/1992 | Munnerlyn | 606/5 |

FOREIGN PATENT DOCUMENTS

| | | | |
|---|---|---|---|
| 0402250 | 12/1990 | European Pat. Off. | 606/17 |
| 63-216566 | 9/1988 | Japan . | |
| 64-58255 | 3/1989 | Japan . | |
| 3-218744 | 9/1991 | Japan . | |

OTHER PUBLICATIONS

Japanese Patent Application Number HEI 2-416767 which corresponds to United States Patent application Serial Number 07/812,819 a copy of the specification of which is filed herewith.

*Primary Examiner*—Angela D. Sykes
*Assistant Examiner*—Sonya Harris-Ogugua
*Attorney, Agent, or Firm*—Finnegan, Henderson, Farabow, Garrett & Dunner, L.L.P.

[57] ABSTRACT

An optical ophthalmic treatment apparatus including an binocular observation optical system to observe an eye to be operated through a stereo microscope and a laser beam transmitting optical system to transmit a therapeutic laser beam emitted from a laser source onto the eye, the laser beam transmitting optical system comprising an irradiation area confining member capable of controlling an aperture diameter thereof, a projective lens for projecting an aperture image of the irradiation area confining member onto an affected part of the eye to be operated, a laser beam reflecting member for reflecting the optical axis of the laser beam transmitting system so as to be coaxial with the optical axis of an objective lens, and a condenser member for condensing the therapeutic laser beam at a position close to the laser beam reflecting member, the condenser member being arranged in the side of the laser source with respect to the irradiation area confining member.

6 Claims, 4 Drawing Sheets dichroic mirror

OPTICAL OPHTHALMIC TREATMENT APPARATUS

This application is a continuation of application Ser. No. 08/016,973, filed Feb. 12, 1993, now abandoned.

BACKGROUND OF THE INVENTION

1. Field of the Invention

The present invention relates to an optical ophthalmic treatment apparatus, and more particularly to an optical ophthalmic treatment apparatus capable of applying a therapeutic laser beam onto an affected part of the eye, while the operator observes the eye to be operated through a stereo microscope.

2. Description of Related Art

A known optical ophthalmic treatment apparatus erodes a surface of a cornea with an excimer laser or the like to change the curvature of the surface of the cornea, whereby the refractive error of the cornea can be corrected. In such apparatus, to irradiate precisely a therapeutic light beam onto the eye, it is preferable that the optical axis of a therapeutic light beam, in a laser beam transmitting optical system within the apparatus, be coaxial with the optical axis of an objective lens in an observation optical system.

A method has been proposed arranging a dichroic mirror in the optical path of the therapeutic light beam.

For example, Japanese Laid-open Patent Application No. SHO 64(1989)-58255 proposes an apparatus providing a particular dichroic mirror which has a characteristic property of reflecting the laser beam from the mirror surface to erode a surface of the cornea, while reflecting the visible rays by upper and lower parts of its reverse portion. The part dichroic mirror is being arranged between the objective lens and the observation device in the well-known binocular observation optical system comprising the objective lens and the observation device, with the dichroic mirror being capable of reflecting infrared radiation by and transmitting the visible rays through the surface which is irradiated by a laser beam. The therapeutic light beam emitted from a laser beam oscillator is reflected by the dichroic mirror, inserted in the optical path of the binocular observation optical system toward the eye which is to be operated upon, and further condensed on the affected part of eye to be operated upon through the objective lens. In this apparatus, after reflected by the eye, the illuminating light for observation is introduced into the binocular observation optical system through the objective lens and the dichroic mirror.

In another proposed method, a total reflecting mirror is arranged in the optical axis of the objective lens to reflect the therapeutic light beam. For example, the apparatus comprising a stereo microscope for operation is shown in Japanese Laid-open Patent Application No. SHO 63(1988)-216566. In this apparatus, a pair of binocular observation optical systems are arranged to share an objective lens, and a total reflecting mirror is disposed on an optical path of the objective lens between the optical axis of each binocular observation optical system. Therefore, by using this apparatus, the front part of the eye, including the cornea as a portion to be operated upon, may be observed stereoscopically through the observing optical system, and the therapeutic light beam may be transmitted onto the affected part of the eye to be operated upon through the total reflecting mirror.

However, there are some problems in these known methods. In the former method using a dichroic mirror, higher apparatus cost results from the use of expensive dichroic mirrors. As shown in FIG. 4, in the case of arranging a dichroic mirror with a suitable inclination (normally 45°) between an objective lens and a target on the patient's eye, astigmatism occurs. Therefore, an aberration compensating lens needs to be arranged in the observation optical system.

In the latter method using a small total reflecting mirror, an observation visual field is unobstructed by the total reflecting mirror because a small mirror may not enter each optical path of right and left eyes of an observing system. In the case of using a larger mirror, the edge of which appears at an inner side of each visual field of the right and left eyes, and a target on the patient's eye may thus not be observed clearly. Accordingly, because of the size of the total reflecting mirror to be employed, a part of the observation visual field is obstructed by the total reflecting mirror, resulting in a partial loss of the visual field.

SUMMARY OF THE INVENTION

The present invention has been made in view of the above circumstances and has an object to overcome the above problems and to provide an optical ophthalmic treatment apparatus capable of keeping the visual field sufficiently in the observing system.

Another object of the present invention is to provide an apparatus that has a simple structure and is low in cost.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the optical ophthalmic treatment apparatus of this invention comprises an binocular observation optical system to observe an eye to be operated upon through a stereo microscope and a laser beam transmitting optical system to transmit a therapeutic laser beam emitted from a laser source onto the eye. The laser beam transmitting optical system comprises an irradiation area confining member capable of controlling an aperture diameter thereof, a projection lens for projecting an aperture image of the irradiation area confining member onto an affected part of the eye to be operated upon, a laser beam reflecting member for reflecting the optical axis of the laser beam transmitting system so as to be coaxial with the optical axis of an objective lens, and a condenser member for condensing the therapeutic laser beam at a position close to the laser beam reflecting member. The condenser member is arranged to the side of the laser source with respect to the irradiation area confining member.

In another aspect of the present invention, an optical ophthalmic treatment apparatus for ablating a surface of a cornea to correct refractive errors of the eye to be operated upon comprises a laser oscillator for emitting a therapeutic laser beam, an irradiation area confining mask for confining an irradiation area on the eye to be operated upon by irradiation of the therapeutic laser beam. A mask projecting lens projects an aperture image of the mask onto a cornea of the eye, and a laser beam reflecting member is arranged on the optical path of the observation optical system for transmitting the light reflected by the eye to be operated upon through the objective lens, and for reflecting the therapeutic laser beam emitted from the laser oscillator toward the eye to be upon. A condenser member is provided for condensing the therapeutic laser beam emitted from the laser oscillator at a position close to the laser reflecting member.

BRIEF DESCRIPTION OF THE DRAWINGS

The accompanying drawings, which are incorporated in and constitute a part of this specification, illustrate an embodiment of the invention and, together with the description, serve to explain the objects, advantages and principles of the invention.

In the drawings.

DETAILED DESCRIPTION OF THE PREFERRED EMBODIMENTS

A detailed description of a first preferred embodiment of an optical ophthalmic treatment apparatus embodying the present invention will now be given referring to the accompanying drawings.

Figure 1:
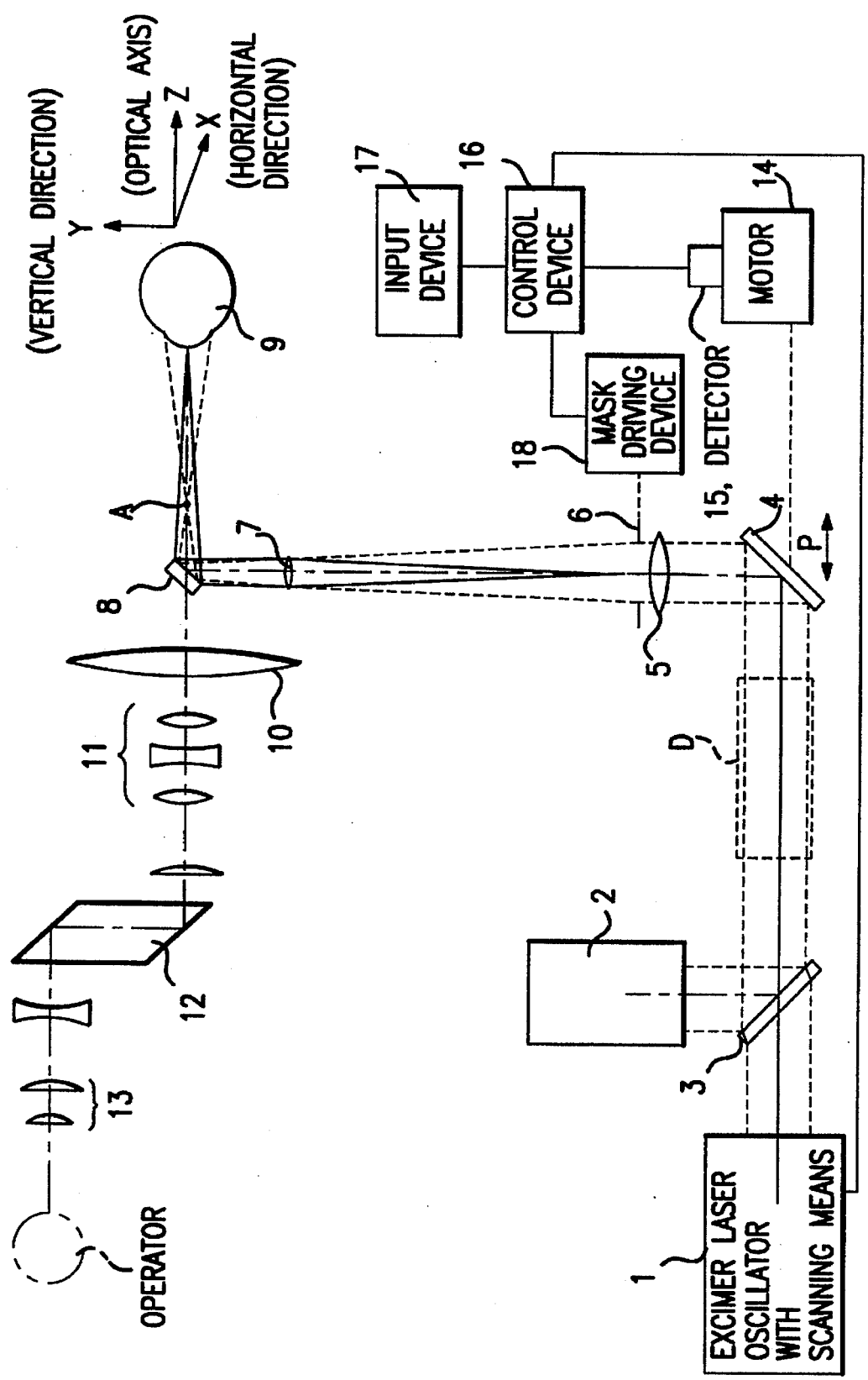
FIG. 1 is a schematic diagram of the arrangement of a first embodiment of an optical system of the present invention.
Figure 2:
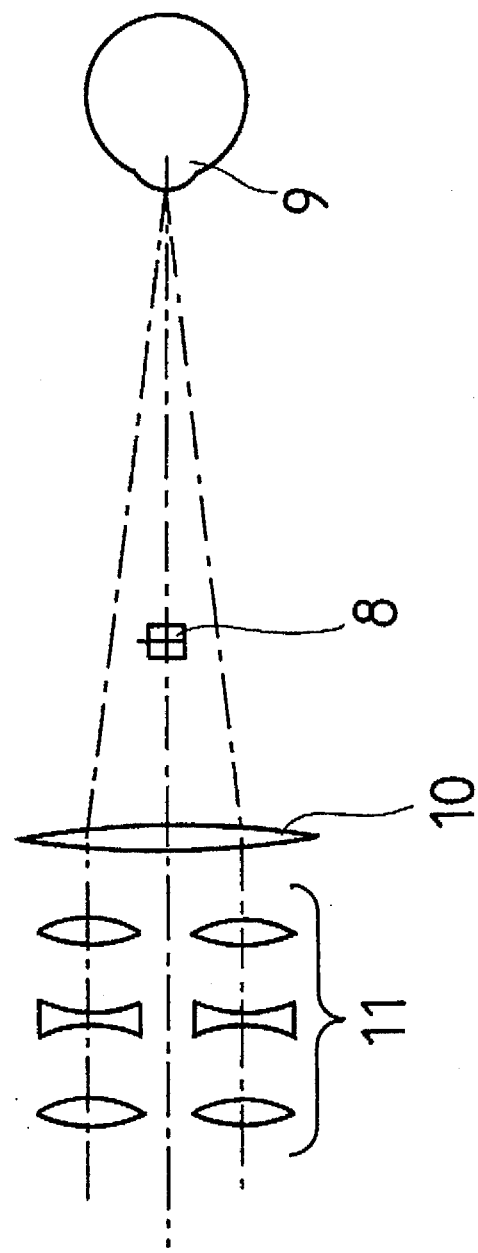
FIG. 2 is a schematic diagram showing a plan of a stereoscopic observation optical system included in the system of FIG. 1.

In FIG. 1, there is shown an arrangement of an optical system in an optical ophthalmic treatment apparatus including an excimer laser as a laser source of a therapeutic laser beam. FIG. 2 shows a schematic plan view of a part of an observation optical system.

As illustrated in FIGS. 1 and 2, an optical system of the optical ophthalmic treatment apparatus includes an excimer laser oscillator 1 for emitting a therapeutic laser beam having a wavelength of 193 nm, a visible diode laser oscillator 2 as a laser source for a guide laser beam, a dichroic mirror 3 to reflect the guide laser beam emitted from the laser oscillator 2 so as to travel coaxially with the therapeutic laser beam emitted from the excimer laser oscillator 1, and a mirror 4 movable in parallel to a direction P. The guide laser beam, being a visible laser beam emitted from the diode laser oscillator 2, is adjusted so as to be a parallel pencil of rays having an area range almost the same as that of the therapeutic laser beam. Further, the guide laser beam is employed to confirm a position to be irradiated by the therapeutic laser beam. When using an ultraviolet rays beam as a therapeutic laser beam, the therapeutic irradiation position may not be confirmed in advance because the ultraviolet rays beam is invisible.

The present embodiment is based on the same principle as an new ablation apparatus for ablating an object by laser beam shown in Japanese Patent Application No. HEI2(1990)-416767 (U.S. patent application Ser. No. 07/812,819) proposed by this applicant. More concretely, when ablating an object by laser beam having a non-uniform beam intensity of Gaussian distribution in one direction and a uniform beam intensity in the vertical direction, it is possible to ablate the object with an almost uniform depth by scanning in a non-uniform beam intensity distribution direction. When employing another method for obtaining a uniform depth of ablation by using a filter having a special transmission factor distribution as shown in JP Publication (Kokai) No. SHO 63(1988)-150069 (U.S. Pat. No. 4,911,711), or by reflecting a laser beam, the optical systems thereof may be arranged in a position indicated by dotted box D. The pencil of rays to be used may be extended.

The apparatus of this embodiment further comprises a mask 6 which directs irradiation of the therapeutic laser beam emitted from the excimer laser oscillator 1 onto a confined area of an eye to be operated upon. A projection lens 7 projects an aperture image of the mask 6 on a cornea 9 of the eye to be operated upon. The mask 6 is capable of changing its aperture diameter by a well-known mechanism so that an irradiation area on the surface of the cornea 9 can be changed.

A reflecting mirror 8 reflects the therapeutic laser beam emitted from the above excimer laser oscillator 1 toward the eye, and is arranged with a suitable inclination on an optical axis of an objective projection lens 10 disposed on optical axis Z of the observation optical system. An 8 mm square mirror is used as the reflecting mirror 8 in this embodiment. Therefore, in view of its size, the optical path of the observation system is not obstructed by the mirror 8. When the mirror 8 is arranged closer to the objective lens 10, a larger mirror may be used for the reflecting mirror 8.

A condenser lens 5 condenses a luminous flux of the therapeutic laser beam on point A via reflecting mirror 8, and is arranged close to a laser source side of the mask 6. Point A is positioned slightly to the eye side of the reflecting mirror 8. Further, although the condensing position of the condenser lens 5 is located at point A in consideration of the strength of the reflecting mirror 8, it is preferable to condense a luminous flux of a laser beam at a reflecting point on the reflecting mirror 8 if the mirror 8 has enough strength to withstand it. The lens power of a condenser lens 5 is determined relative to the projection lens 7.

An observation optical system comprises an objective lens 10, a pair of zooming optical systems 11, a pair of prisms 12, and a pair of eyepieces 13 for right and left eyes respectively.

A control system of the apparatus is explained as follows. The plane mirror 4 of FIG. 1 is movable parallel to the optical axis of a laser beam by a driving motor 14, and the position of the mirror 4 (amount of movement) is detected by a positioning detector 15. The positioning detector 15 may comprise, for example, a rotary encoder attached to a driving axis of the mirror's driving motor 14.

The position detector 15 and the laser source 1 are connected to a control device 16, and the laser pulses are emitted based on an output signal of the positioning detector 15. The operation of the present apparatus is controlled by a microcomputer of the control device 16. That is, an input device 17 is connected to the control device 16, and datum including radius of curvature of the pre-ablation cornea, correction power of an eye, and the depth of the ablation to be taken place or the like, are inputted to the control device 16 via the input device 17.

A mask driving device 18 changes an aperture diameter of the mask 6, and, for this purpose is connected to the control device 16. The diameter of the mask 6 is changed based on an output signal of the control device 16.

According to the above apparatus, the ophthalmic treatment operation is explained as follows. First, the operator observes the eye to be operated upon through the pair of eyepieces 13 to so that an eye can be positioned in X-Y-Z direction so as to be located at a desired position. The position and depth of ablation, calculated in advance based on an extent of refractive errors and a cornea shape or the like, is inputted into the microcomputer of the control device 16. Accordingly, based on the data, the operation of an excimer laser oscillator 1, a mirror 4 and a mask 6 and others are controlled by the microcomputer of the control device 16.

A therapeutic laser beam emitted from the excimer laser oscillator 1 is reflected by the mirror 4, and condensed by a condenser lens 5. After transmission through the mask 6 and the projective lens 7, the therapeutic laser beam is reflected by a reflecting mirror 8 toward the eye, and condensed at point A. The aperture image of the mask 6 is projected on the cornea 9 of the eye to be operated upon through a projection lens 7, whereby the surface of the cornea 9 is ablated. During the operation, the mirror 4 is moved in turn in parallel to the P-direction per one shot by a driving motor 14 so that the therapeutic laser beam may transmit through an aperture of a mask 6 uniformly.

In the binocular observation optical system, the light beam reflected by the cornea 9 is conducted to the right and left zooming optical systems 11, 11 through the objective lens 10, and reflected toward the pair of eyepieces 13, respectively, by the right and left prisms 12 whereby the operator may observe the patient's eye.

Normally, because an excimer laser beam has an extraordinary sectional area of the luminous flux (about 10 times) compared with that of the general gas laser, e.g. helium, neon, argon laser and the like, a total reflecting mirror (as a reflecting mirror 8) should be provided in an observation optical system. Accordingly, in the present invention, a small mirror can be employed as the reflecting mirror 8 by arranging the condenser lens 5 to reduce the diameter of luminous flux, so that a visual field of the observation system may be kept sufficient without any lack of clarity.

When the operator observes an affected part of the patient's eye directly in a condition that a microscope for observation is left close to the affected part (target) of the patient's eye, in a known microscope using a usual dichroic mirror and the like, a distance from the dichroic mirror to the target is short because of a diameter of luminous flux being large, whereby the microscope is obstructive to the observation of the operator. On the other hand, in the present invention employing a microscope miniaturized by using a small reflecting mirror because of a luminous flux which is reduced through a condenser lens, a distance from the dichroic mirror to a target may be kept longer. Therefore, the microscope will not obstruct the operator's observation.

Figure 3:
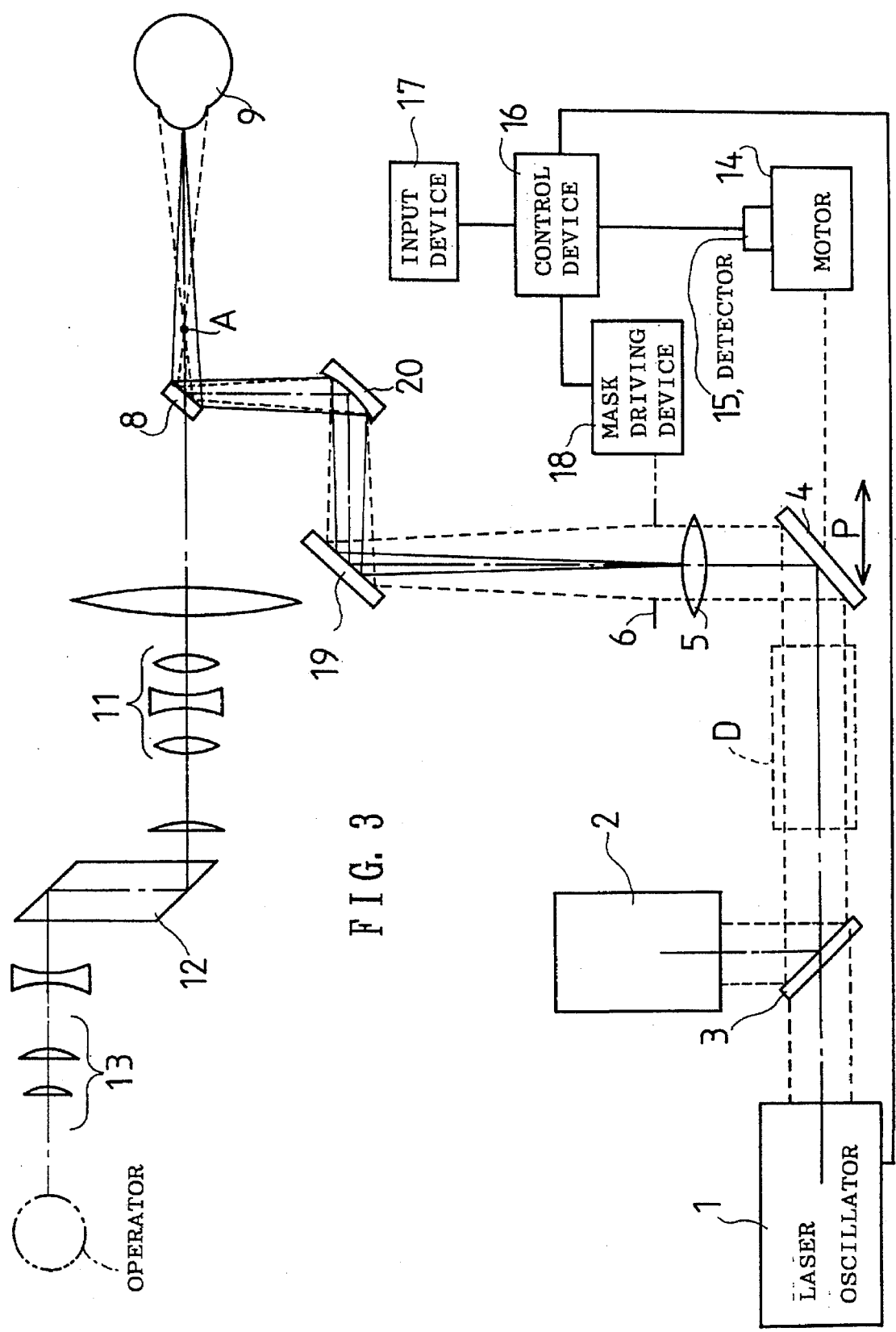
FIG. 3 is a schematic diagram of the arrangement of another optical system that forms a second embodiment of the present invention.
Figure 4:
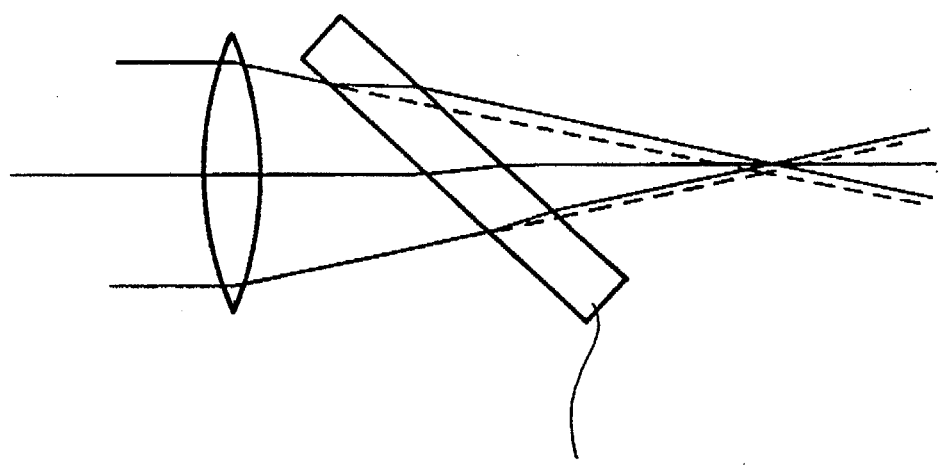
FIG. 4 is a schematic diagram illustrating a prior art observation optical system that requires an aberration compensating lens for astigmatism.

Further, in another embodiment of the present invention referring to FIG. 3, a reflector 19 and a concave condenser mirror 20 are arranged on an optical path to transmit a therapeutic laser beam emitted from excimer laser oscillator 1 toward reflecting mirror 8. The reflector 19 deflects a luminous flux transmitted through mask 6 toward the concave condenser mirror 20, and the luminous flux reflected by a reflector 19 is condensed onto a surface of a reflecting mirror 8 by the concave condenser mirror 20. According to the present embodiment, the same effect can be obtained as described for the first embodiment, that is, a small mirror can be used for the reflecting mirror 8, whereby a visual field of an observation system may be kept sufficient without any lack of clarity and also a microscope can be miniaturized.

The present invention may be embodied in other specific forms without departing from the spirit or essential characteristics thereof. For instance, although the embodiment using an excimer laser beam as a therapeutic laser beam is explained, it is possible to apply another therapeutic laser beam.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic treatment apparatus comprising:

a binocular observation optical system having right and left observation optical paths for observing an eye to be operated upon through use of a stereo microscope;

a laser beam transmitting optical system to transmit a therapeutic laser beam onto the eye;

said laser beam transmitting optical system having:

a laser source for generating an ultraviolet therapeutic laser beam;

an irradiation area confining member having an aperture which has a controllable diameter and through which the therapeutic laser beam is transmitted from said laser source;

a projection lens for projecting an aperture image of the therapeutic laser beam transmitted from said irradiation area confining member as an aperture image onto an affected part of the eye to be operated on;

a laser beam reflecting member disposed between the right observation optical path and the left observation optical path to reflect the therapeutic laser beam of said laser beam transmitting system so that the therapeutic laser beam is directed from the projecting lens along a laser beam axis coaxial with an optical axis of an objective lens in said observation optical path;

said laser beam reflecting member being sufficiently small to be substantially non-obstructive to said right and left observation optical paths; and a condenser member disposed at a position in a path of the therapeutic laser beam upstream from said irradiation confining member yet close to said laser beam reflecting member, said condenser member reducing a diameter of luminous flux of the therapeutic laser beam and directing the therapeutic laser beam through said irradiation confining member for reflection from the laser beam reflection member to the eye, said condenser member sufficiently reducing a diameter of luminous flux of the therapeutic laser beam to enable said laser beam reflecting member to be sufficiently small as defined.

2. The apparatus according to claim 1, wherein said condenser member consists of a condenser lens.

3. The apparatus according to claim 1, wherein said laser source comprises an excimer laser oscillator.

4. An optical ophthalmic treatment apparatus for ablating surface of a cornea to correct a refractive error of the eye to be operated upon, comprising:

a laser oscillator for emitting an ultraviolet therapeutic laser beam along a therapeutic optical path with sufficient energy for ablation;

an irradiation area confining mask for confining an irradiation area on the eye to be operated upon through irradiation by said therapeutic laser beam;

a mask projecting lens for projecting an aperture image of said mask onto a cornea of the eye;

a laser beam reflecting member disposed in an observation optical system having an objective lens for transmitting observation light reflected from the eye to be operated upon; said laser beam reflecting member further being disposed for reflecting said therapeutic laser beam emitted from said laser oscillator along the therapeutic optical path toward the eye to be operated upon and being sufficiently small to be substantially non-obstructive to said observation optical path; and a condenser member for condensing said therapeutic laser beam emitted from said laser oscillator at a position close to said laser beam reflecting member thereby enabling said laser beam reflecting member to be sufficiently small in size as defined.

5. The apparatus according to claim 4, wherein said laser oscillator comprises an excimer laser.

6. The apparatus according to claim 4, wherein said condenser member consists of a condenser lens.

* * * * *